US008421857B2

United States Patent
Akao et al.

(10) Patent No.: US 8,421,857 B2
(45) Date of Patent: Apr. 16, 2013

(54) INSPECTION DEVICE OF PLUGGED HONEYCOMB STRUCTURE AND INSPECTION METHOD OF PLUGGED HONEYCOMB STRUCTURE

(75) Inventors: Takayoshi Akao, Nagoya (JP); Akihiro Mizutani, Ichinomiya (JP); Kensuke Tanaka, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 523 days.

(21) Appl. No.: 12/718,221

(22) Filed: Mar. 5, 2010

(65) Prior Publication Data

US 2010/0238281 A1    Sep. 23, 2010

(30) Foreign Application Priority Data

Mar. 23, 2009   (JP) .................................. 2009-069363
Feb. 5, 2010    (JP) .................................. 2010-023749

(51) Int. Cl.
*H04N 7/18*      (2006.01)

(52) U.S. Cl.
USPC .......................................................... 348/92

(58) Field of Classification Search ..................... 348/92
See application file for complete search history.

(56) References Cited

U.S. PATENT DOCUMENTS

| 5,315,375 | A  | * | 5/1994  | Allen ............................. 356/417 |
| 5,463,462 | A  | * | 10/1995 | Ohnishi et al. ................ 356/521 |
| 7,366,340 | B1 | * | 4/2008  | Smithgall ..................... 382/141 |
| 8,234,909 | B2 | * | 8/2012  | Suman et al. ..................... 73/38 |
| 2007/0238191 | A1 | * | 10/2007 | Gargano et al. ............... 436/164 |

FOREIGN PATENT DOCUMENTS

| JP | 58-155343   | A1 |   | 9/1983  |
| JP | 05-264459   | A1 |   | 10/1993 |
| JP | 2006-200957 | A1 |   | 8/2006  |
| JP | 2006200957  | A  | * | 8/2006  |
| JP | 2008-058116 | A1 |   | 3/2008  |

* cited by examiner

*Primary Examiner* — Sath V Perungavoor
*Assistant Examiner* — Jeffrey Williams
(74) *Attorney, Agent, or Firm* — Burr & Brown (57) ABSTRACT

There is disclosed an inspection device of a plugged honeycomb structure in which a plugged honeycomb structure is an inspection target, and the inspection device comprises a light source which illuminates one end face of the plugged honeycomb structure as the inspection target; a camera-side lens which condenses light emitted from the light source to the one end face, transmitted through plugged portions of the plugged honeycomb structure and radiated from the other end face; a camera which receives the light condensed by the camera-side lens; and an image processor which processes an image of the light received by the camera to display the contrast of the light transmitted through the plugged portions of the plugged honeycomb structure.

8 Claims, 9 Drawing Sheets

INSPECTION DEVICE OF PLUGGED HONEYCOMB STRUCTURE AND INSPECTION METHOD OF PLUGGED HONEYCOMB STRUCTURE

BACKGROUND OF THE INVENTION

1. Field of the Invention

The present invention relates to an inspection device of a plugged honeycomb structure and an inspection method of the plugged honeycomb structure. More particularly, it relates to an inspection device of a plugged honeycomb structure which can efficiently and simultaneously inspect the depths and defects of plugged portions, and an inspection method of the plugged honeycomb structure.

2. Description of the Related Art

In various fields of chemistry, electric power, iron and steel and the like, a ceramic honeycomb structure which is excellent in heat resistance and corrosion resistance is employed as a carrier for a catalyst device and a filter used for an environmental countermeasure, the collection of a specific material or the like. The honeycomb structure is a cylindrical structure having partition walls which partition a plurality of cells extending from one end face to the other end face of the structure. Especially in recent years, a plugged honeycomb structure has been developed by alternately plugging open frontal areas of cells in both end faces of the honeycomb structure, and has frequently been used as a diesel particulate filter (DPF) which collects a particulate matter (PM) discharged from a diesel engine or the like.

In such a plugged honeycomb structure, plugged portions uniformly have a predetermined constant depth. This is because if the depths of the plugged portions are small dimensions, the plugged portions easily break down. If the depths of the plugged portions are large, a pressure loss increases, and a filter area of the structure as the filter decreases. To solve such a problem, a method for measuring the depths of the plugged portions of the plugged honeycomb structure is suggested (e.g., see JP-A-2008-58116).

SUMMARY OF THE INVENTION

In a measuring method of the depths of plugged portions of plugged honeycomb structure described in JP-A-2008-58116, an inspection rod is inserted into an open frontal area of each cell, and the height of the inspection rod projecting from the cell is measured. This method has a problem that the inspection rod is inserted into the plugged portions one by one and hence an excessively long measurement time is required for the inspection of all the plugged portions, and a problem that a work might break down owing to the measurement method of a contact type.

On the other hand, in the plugged honeycomb structure, the plugged portions preferably do not have any defect such as a pinhole or a crack. If the pinholes, cracks and the like are formed in the plugged portions, the collecting function of the filter lowers. In the above invention described in JP-A-2008-58116, the depths of the plugged portions can be measured, but the pinholes and the like of the plugged portions cannot be detected.

The present invention has been developed in view of the above problems, and an object thereof is to provide an inspection device of a plugged honeycomb structure which can simultaneously inspect the depths and defects of plugged portions of the plugged honeycomb structure for a short time and in a non-contact manner, and an inspection method of the plugged honeycomb structure.

To achieve the above object, according to the present invention, there are provided the inspection device of the plugged honeycomb structure and the inspection method of the plugged honeycomb structure as follows.

[1] An inspection device of a plugged honeycomb structure in which the cylindrical plugged honeycomb structure having porous partition walls to partition a plurality of cells extending through the structure from one end face to the other end face thereof and having plugged portions at the ends of the cells is an inspection target, the inspection device comprising: a light source which illuminates the one end face of the plugged honeycomb structure as the inspection target; a camera-side lens which condenses light emitted from the light source to the one end face, transmitted through the plugged portions of the plugged honeycomb structure and radiated from the other end face; a camera which receives the light condensed by the camera-side lens; and an image processor which processes an image of the light received by the camera to display the contrast of the light transmitted through the plugged portions of the plugged honeycomb structure.

[2] The inspection device of the plugged honeycomb structure according to the above [1], further comprising: a field lens disposed between the honeycomb structure and the camera-side lens to condense, toward the camera-side lens, the light transmitted through the plugged portions of the honeycomb structure and radiated from the other end face, wherein the light condensed by the field lens is further condensed by the camera-side lens, and received by the camera.

[3] The inspection device of the plugged honeycomb structure according to the above [2], further comprising: an X-Y moving stage to which the camera and the camera-side lens are attached and which moves the camera and the camera-side lens in a plane substantially parallel to the end face of the plugged honeycomb structure on such a side as to radiate the light.

[4] The inspection device of the plugged honeycomb structure according to the above [2] or [3], wherein a relation of "D/f>0.034" is established in which D is the effective diameter of the camera-side lens, and f is the focal length of the field lens.

[5] The inspection device of the plugged honeycomb structure according to any one of the above [1] to [4], wherein the light emitted from the light source to the one end face of the plugged honeycomb structure is light which spreads at a specific radiation angle, and the radiation angle has a size which is not less than an angle formed by a line crossing the one end face of the plugged honeycomb structure at right angles and the cells.

[6] The inspection device of the plugged honeycomb structure according to the above [5], wherein the radiation angle is 10° or less.

[7] An inspection method of the plugged honeycomb structure which inspects the depths and defects of the plugged portions of the plugged honeycomb structure by use of the inspection device of the plugged honeycomb structure according to any one of the above [1] to [6].

According to the inspection device of the plugged honeycomb structure of the present invention, the light transmitted through the plugged portions of the plugged honeycomb structure is condensed by the camera-side lens, and the condensed light is received by the camera, whereby the contrast of the light can be displayed by image processing. Therefore, the depths and defects of the plugged portions can be inspected for a short time and in a non-contact manner. The plugged portions have different light transmittances depending on the depths thereof, and hence the depths of the plugged portions can be detected by the contrast (luminance) of the light represented by the image processing. Furthermore, if defects occur in the plugged portions, the amount of the transmitted light becomes very large. Therefore, the defects of the plugged portions can be detected by the contrast (luminance) of the light represented by the image processing.

According to the inspection method of the plugged honeycomb structure of the present invention, the depths and defects of the plugged portions of the plugged honeycomb structure are inspected by using the above inspection device of the plugged honeycomb structure of the present invention, whereby the depths and defects of the plugged portions can be inspected for a short time and in a non-contact manner.

DESCRIPTION OF REFERENCE NUMERALS

1: light source, 2: camera-side lens, 3: camera, 4: image processor, 11: field lens, 12: X-Y moving stage, 21: field lens integral type camera, 31: plugged honeycomb structure, 32: partition wall, 33: plugged portion, 34: cell, 35: one end face, 36: the other face, 41, 42 and 43: state of light transmitted through plugged portions, 100, 200 and 300: inspection device of plugged honeycomb structure, α: radiation angle, and β: angle at which light emitted from light source spreads.

DETAILED DESCRIPTION OF THE INVENTION

Next, embodiments of the present invention will be described in detail with reference to the drawings, but it should be understood that the present invention is not limited to the following embodiments and that alternations, modifications and the like of design should appropriately be added based on the ordinary knowledge of a person with ordinary skill in the art without departing from the scope of the present invention.

Figure 1:
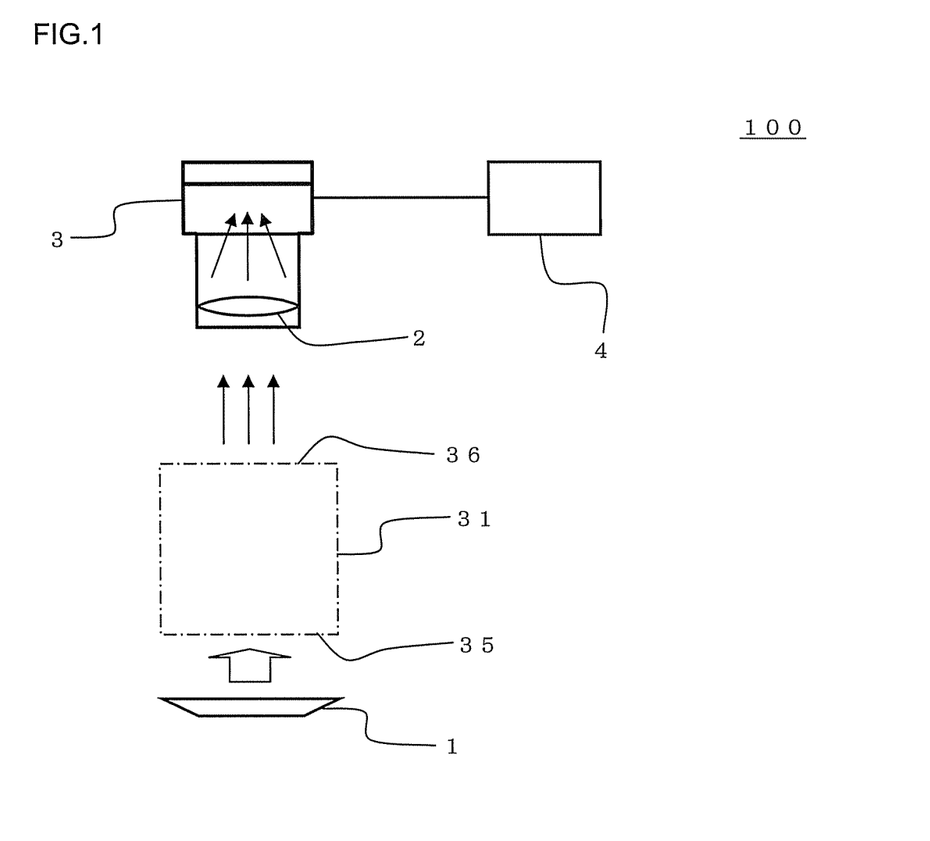
FIG. 1 is a schematic diagram showing one embodiment of an inspection device of a plugged honeycomb structure of the present invention.
Figure 5A:
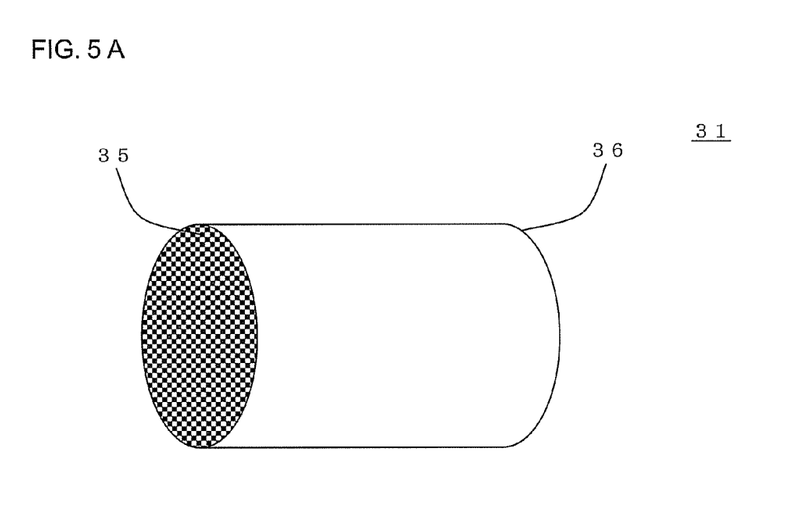
FIG. 5A is a perspective view schematically showing the plugged honeycomb structure which is an inspection target of the inspection device of the plugged honeycomb structure of the present invention.
Figure 5B:
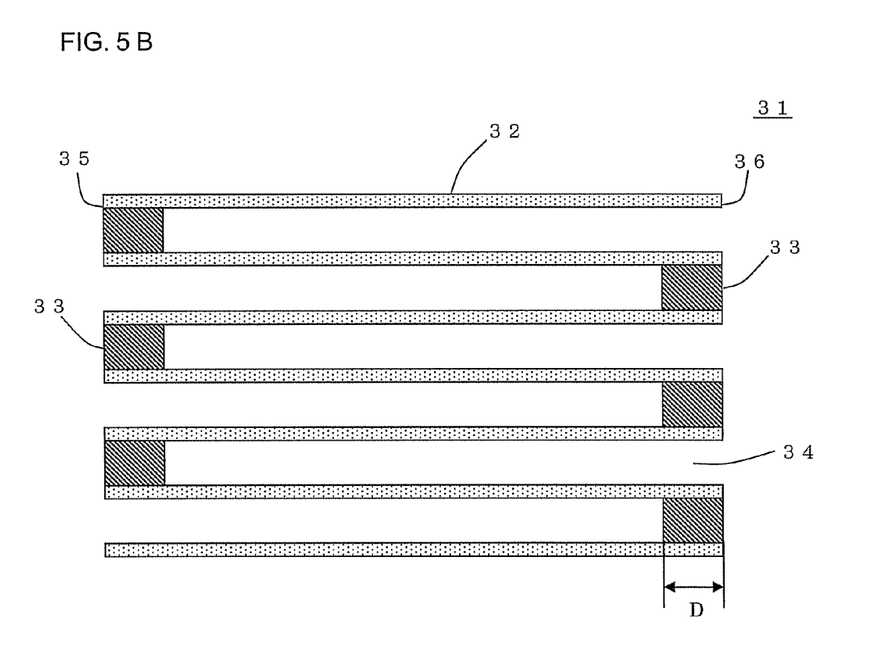
FIG. 5B is a schematic diagram schematically showing a part of the plugged honeycomb structure which is the inspection target of the inspection device of the plugged honeycomb structure of the present invention, that is, showing the cross section of the structure parallel to a central axis.

1. Inspection Device of Plugged Honeycomb Structure:

In one embodiment of an inspection device of a plugged honeycomb structure of the present invention, as shown in FIGS. 5A and 5B, a cylindrical plugged honeycomb structure 31 having porous partition walls 32 which partition a plurality of cells 34 extending through the structure from one end face 35 to the other end face 36 thereof and having plugged portions 33 at the ends of the cells 34 is an inspection target. Depths D of the plugged portions of the plugged honeycomb structure are lengths of the plugged portions 33 in a direction in which the cells 34 extend as shown in FIG. 5B. Moreover, in the inspection device of the plugged honeycomb structure of the present invention, the plugged honeycomb structure having a radius of a cross section thereof crossing a central axis direction at right angles in a range of 50 to 500 mm and having a length thereof in the central axis direction in a range of 40 to 500 mm is preferably the inspection target (there is not any special restriction on the shape of the cross section, and the shape may be, for example, an elliptic, quadrangular or triangular shape or the like). Moreover, as shown in FIG. 1, an inspection device 100 of the plugged honeycomb structure of the present embodiment comprises a light source 1 which illuminates the one end face 35 of the plugged honeycomb structure 31 as the inspection target; a camera-side lens 2 which condenses light emitted from the light source 1 to the one end face 35, transmitted through the plugged portions of the plugged honeycomb structure 31 and radiated from the other end face 36; a camera 3 which receives the light condensed by the camera-side lens 2; and an image processor 4 which processes an image of the light received by the camera 3 to display the contrast (luminance) of the light transmitted through the plugged portions of the plugged honeycomb structure 31. In FIG. 1, arrows directed from the light source to the camera indicate the proceeding of the light, and this also applies to FIGS. 2, 3A and 3B. FIG. 5A is a perspective view schematically showing the plugged honeycomb structure which is the inspection target of the inspection device of the plugged honeycomb structure of the present invention. FIG. 5B is a schematic diagram schematically showing a part of the plugged honeycomb structure which is the inspection target of the inspection device of the plugged honeycomb structure of the present invention, that is, showing the cross section of the structure parallel to a central axis. FIG. 1 is a schematic diagram showing the embodiment of the inspection device of the plugged honeycomb structure of the present invention.

In this way, in the inspection device of the plugged honeycomb structure of the present embodiment, the light emitted from the light source to the honeycomb structure and transmitted through the plugged portions is condensed by the camera-side lens, and the image of the light is received by the camera and processed by the image processor, whereby the depth of the plugged portions and the defects (plugged state) of the plugged portions can be inspected for a short time and in a non-contact manner.

In the inspection device of the plugged honeycomb structure of the present embodiment, there is not any special restriction on the light source, but the light source is preferably a diffusion light source which is bright at such a level as to detect an abnormal portion. Moreover, there is not any special restriction on the light source, but the light source preferably keeps a uniform illuminance in a plane to prevent bright unevenness of a signal depending on a place. The light source is disposed at such a position as to illuminate the one end face of the plugged honeycomb structure, and the light source and the one end face of the plugged honeycomb structure may come in contact or may be disposed away from each other. In a case where they are disposed away from each other, the brightness of the signal lowers owing to the decrease of the amount of the light as compared with a case where they come in contact. Therefore, the amount of the illuminative light may be increased.

Figure 9:
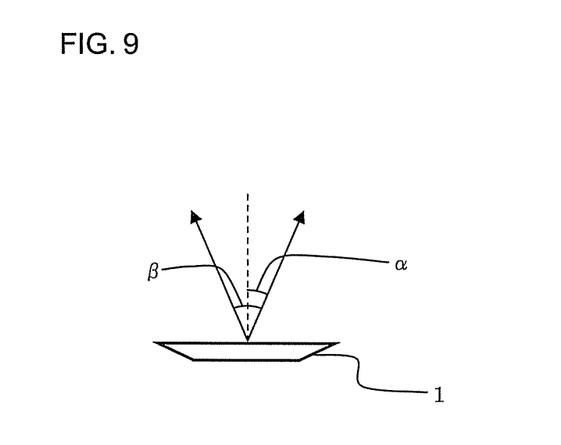
FIG. 9 is a schematic diagram showing the spread of the light emitted from a light source.

Moreover, the light emitted from the light source to the one end face of the plugged honeycomb structure is preferably light which spreads at a specific radiation angle $\alpha$, and the radiation angle $\alpha$ has a size which is not less than an angle $\theta$ formed by a line crossing the one end face of the plugged honeycomb structure at right angles and the cells (the cells of the plugged honeycomb structure). Since the angle (the radiation angle) of the light emitted from the light source is such an angle, the light from the light source can securely pass through the cells which tilt as much as the angle $\theta$, and hence the defects of the plugged portions can securely be inspected. If the radiation angle $\alpha$ is smaller than the angle $\theta$, the light from the light source cannot securely pass through the cells which tilt as much as the angle $\theta$ sometimes, and the defects of the plugged portions are not easily inspected sometimes. The "radiation angle $\alpha$" of the light from the light source is an angle having a size of ½ of an angle $\beta$ at which the light emitted from the light source 1 spreads as shown in FIG. 9. FIG. 9 is a schematic diagram showing the spread of the light emitted from the light source 1. In FIG. 9, "arrows" indicate the light emitted from the light source 1.

Furthermore, the radiation angle $\alpha$ preferably has a size of 10° or less, further 5° or less, and especially preferably has a size (an equal size) of one times the angle formed by "the line crossing the one end face of the plugged honeycomb structure at right angles" and "the cells (the cells of the plugged honeycomb structure)". Since the radiation angle $\alpha$ has such a size, the intensity of the light from the light source does not weaken, and hence the defects of the plugged portions can securely be inspected. If the radiation angle $\alpha$ is larger than 10°, the light from the light source excessively spreads, the intensity of the light weakens, and the defects of the plugged portions are not easily inspected sometimes.

In the inspection device of the plugged honeycomb structure of the present embodiment, the camera-side lens condenses, toward the camera, the light emitted from the light source and transmitted through the plugged portions of the plugged honeycomb structure. When the honeycomb structure is disposed between the camera-side lens and the light source, the camera-side lens is preferably disposed at a focused position in a region from the one end face 35 to the other end face 36. When the camera focuses around the one end face 35, plug defects present in the plugged portions 33 disposed in the one end face 35 can more clearly be picked. Moreover, when the camera focuses around the other end face 36, plug defects present in the plugged portions 33 disposed in the other end face 36 can more clearly be picked. When the center between the one end face 35 and the other end face 36 is focused, the plug defects present in the one end face 35 and the other end face 36 can be evaluated with an equal signal level.

In the inspection device of the plugged honeycomb structure of the present embodiment, the camera preferably has a high sensitivity and a large dynamic range. The camera receives the light condensed by the camera-side lens.

In the inspection device of the plugged honeycomb structure of the present embodiment, the image processor is required to comprise a display unit which can display the picked image. In addition, the image processor preferably has a function of calculating and displaying the contrast of the picked image, which enables quantitative evaluation.

Figure 2:
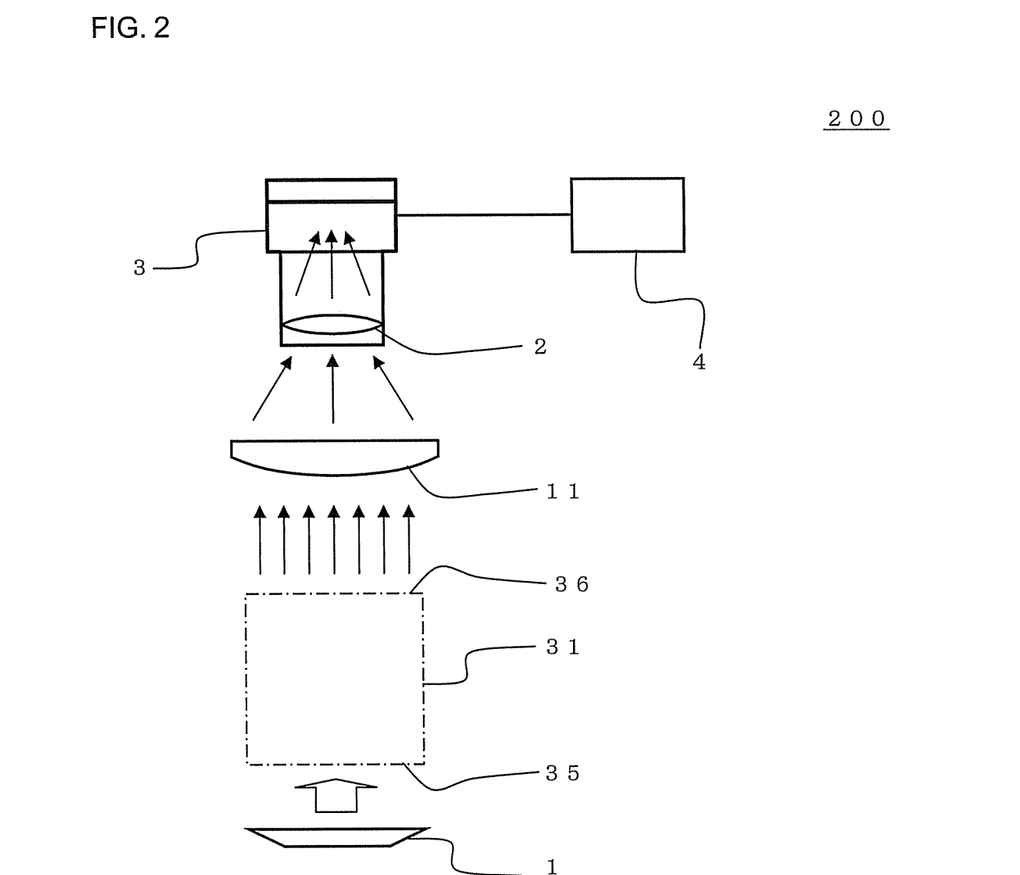
FIG. 2 is a schematic diagram showing another embodiment of the inspection device of the plugged honeycomb structure of the present invention.

In another embodiment of the inspection device of the plugged honeycomb structure of the present invention, as shown in FIG. 2, the inspection device further comprises a field lens 11 disposed between the honeycomb structure 31 and the camera-side lens 2 to condense, toward the camera-side lens 2, the light transmitted through the plugged portions of the honeycomb structure 31 and radiated from the other end face 36. The light condensed by the field lens 11 is further condensed by the camera-side lens 2, and received by the camera. Constituent elements other than the field lens 11 are the same as those of the above embodiment of the inspection device of the plugged honeycomb structure of the present invention. FIG. 2 is a schematic diagram showing the embodiment of the inspection device of the plugged honeycomb structure of the present invention.

In the above embodiment of the inspection device of the plugged honeycomb structure of the present invention, it is not easy to collect, only by the camera-side lens, all the light radiated from the other end face of the plugged honeycomb structure. This reason is that owing to the influence of the field angle of the camera-side lens, the light substantially parallel to an optical axis extending out of the plugged honeycomb structure cannot be grasped over the whole end face. Therefore, when the only camera-side lens is used, inspections are preferably performed as much as a plurality of times while changing an inspection region in the end face of the plugged honeycomb structure. On the other hand, when the field lens is disposed between the plugged honeycomb structure and the camera-side lens, the light radiated from a broader region of the other end face of the camera-side lens can be condensed by the camera-side lens through the field lens. Moreover, since the light condensed by the camera-side lens is further condensed by the camera, the light radiated from the broader region of the other end face of the plugged honeycomb structure is received by the camera, whereby a view field broadens, and the number of the inspection times can be decreased.

In the inspection device of the plugged honeycomb structure of the present embodiment, there is not any special restriction on the shape of the field lens, but a plano-convex lens having a round outer peripheral shape or the like is preferable. Here, "the plano-convex lens" is a lens having one surface which is a flat surface and the other surface which is a convex surface. Here, the effective diameter of the field lens needs to be larger than that of the camera-side lens 2. Moreover, the effective diameter of the field lens is preferably from 50 to 500 mm. If the effective diameter is excessively small, the view field narrows, and the number of the inspection times increases sometimes. Moreover, if the effective diameter is excessively large, the weight of the lens increases, and a mechanism for supporting the lens becomes excessively large. Moreover, the focal length of the field lens is preferably from 40 to 2000 mm. If the focal length is excessively short, the honeycomb structure comes in contact with the field lens, and the condensing lens 2 might break down. If the focal length is excessively large, the size of the device becomes excessively large.

Figure 4:
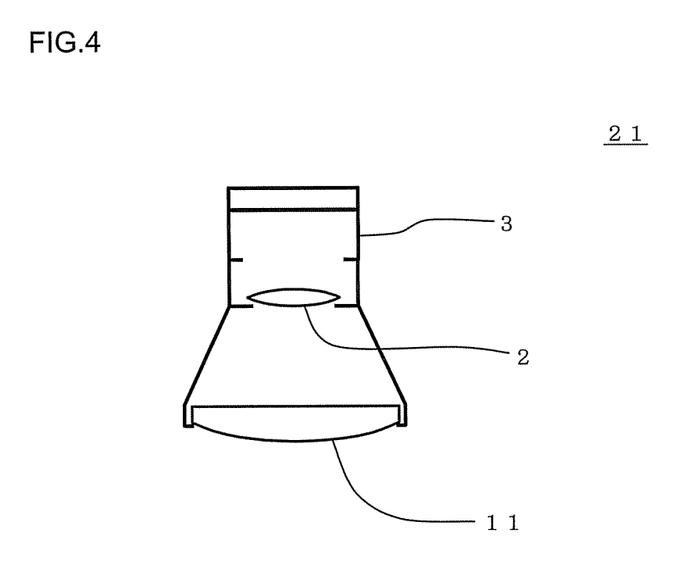
FIG. 4 is a schematic diagram showing a cross section of a field lens integral type camera constituting the inspection device of the plugged honeycomb structure of the present invention.

In the inspection device of the plugged honeycomb structure of the present embodiment, as shown in FIG. 4, a field lens integral type camera 21 may be used in which the camera 3, the camera-side lens 2 and the field lens 11 are integrally formed. The field lens integral type camera 21 is formed so that the camera 3, the camera-side lens 2 and the field lens 11 are fixed while holding preferable positional relations, respectively. FIG. 4 is a schematic diagram showing a cross section of the field lens integral type camera constituting the inspection device of the plugged honeycomb structure of the present invention. Moreover, a configuration may be used in which two or more lenses are used for the correction of aberration.

Figure 3A:
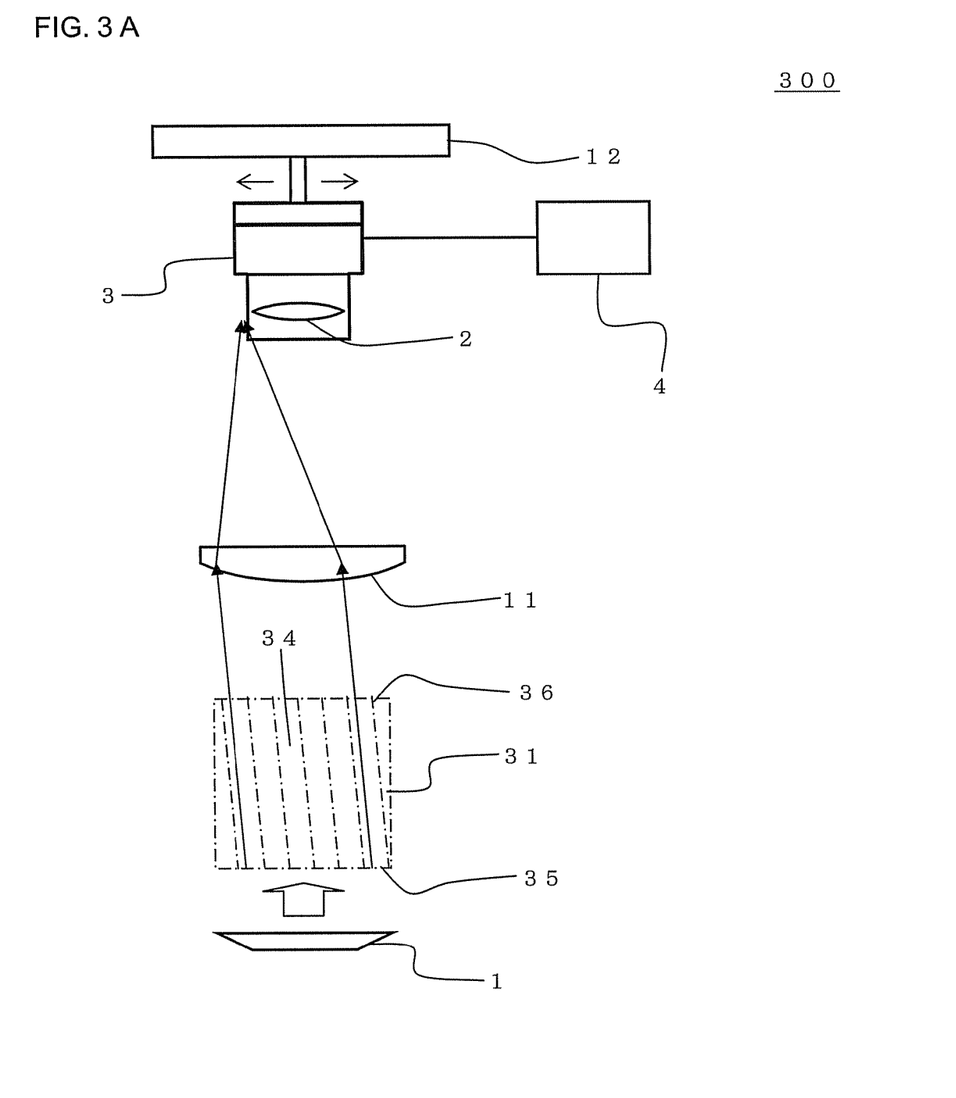
FIG. 3A is a schematic diagram showing still another embodiment of the inspection device of the plugged honeycomb structure of the present invention.
Figure 3B:
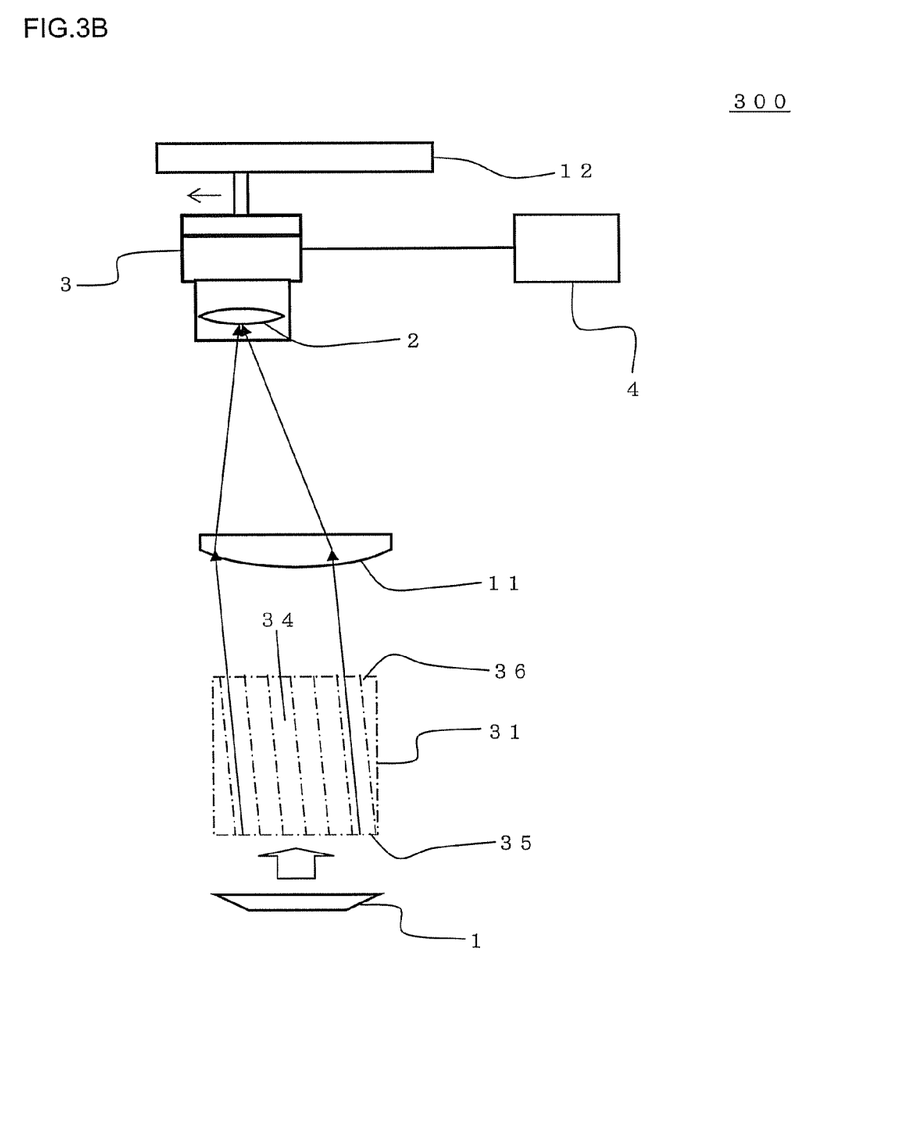
FIG. 3B is a schematic diagram showing the embodiment of the inspection device of the plugged honeycomb structure of the present invention.

In still another embodiment of the inspection device of the plugged honeycomb structure of the present invention, as shown in FIGS. 3A and 3B, the above embodiment of the inspection device of the plugged honeycomb structure of the present invention shown in FIG. 2 further comprises an X-Y moving stage 12. The X-Y moving stage 12 is a device to which the camera 3 and the camera-side lens 2 are attached and which moves the camera 3 and the camera-side lens 2 in a plane substantially parallel to the end face (the other end face 36) of the plugged honeycomb structure 31 on such a side as to radiate the light. In an inspection device 300 of the plugged honeycomb structure of the present embodiment, the camera-side lens 2 and the camera 3 are integrally formed. FIG. 3A is a schematic diagram showing the embodiment of the inspection device of the plugged honeycomb structure of the present invention, and FIG. 3B is a schematic diagram showing the embodiment of the inspection device of the plugged honeycomb structure of the present invention.

The plugged honeycomb structure which is the inspection target of the inspection device of the plugged honeycomb structure of the present invention can be obtained by kneading and extruding a ceramic material containing, for example, predetermined ceramic powder, water and the like to prepare a formed honeycomb article having a honeycomb shape; and alternately forming the plugged portions at the ends of the cells of the obtained formed honeycomb article (both the end faces of the formed honeycomb article have a checkered pattern, each cell has an only one end provided with a plugged portion), formed by firing. Moreover, the obtained plugged honeycomb structure is a porous ceramic article, and the plugged portions are also made of a porous ceramic material similar to that of the partition walls. In such a plugged honeycomb structure, the cells preferably extend along the central axis of the plugged honeycomb structure (hereinafter referred to simply as "the central axis" sometimes), and both the end faces of the structure are formed perpendicularly to the central axis. However, the cells may be formed so as to tilt slightly with respect to the central axis or both the end faces of the structure may be formed at an angle which is not perpendicular to the central axis. The plugged honeycomb structure 31 shown in FIG. 3A is an example in which the cells 34 tilt slightly (about 1°) with respect to the central axis, and both the end faces of the structure are formed perpendicularly to the central axis.

In this way, the plugged honeycomb structure 31 including the cells 34 formed so as to tilt with respect to the central axis is the inspection target. In a case where a plugged state is inspected by the inspection device of the plugged honeycomb structure of the present embodiment, since the cells 34 are tilted, the light from the light source proceeds through the plugged honeycomb structure in a direction which tilts with respect to the central axis direction, and the light radiated from the other end face 36 proceeds in a direction which tilts with respect to the central axis direction. Therefore, as shown in FIG. 3A, the light radiated from the other end face 36 of the plugged honeycomb structure 31, which should be condensed toward the camera-side lens 2 by the field lens 11, proceeds away from the camera-side lens 2, and is not condensed by the camera-side lens 2 sometimes.

On the other hand, as shown in FIG. 3B, the inspection device of the plugged honeycomb structure of the present embodiment comprises the field lens 11 and the X-Y moving stage 12. Therefore, even when the light is radiated from the other end face 36 in the tilted direction, the camera 3 and the camera-side lens 2 are moved by the X-Y moving stage 12, and the light condensed by the field lens 11 does not proceed away from the camera-side lens 2, and can be condensed toward the camera-side lens 2. In consequence, even in a case where the cells are formed so as to slightly tilt with respect to the central axis and both the end faces of the structure are formed at the angle which is not perpendicular to the central axis, the light radiated from the other end face of the plugged honeycomb structure is received by the camera, and the plugged state (the depths and defects of the plugged portions) can be inspected. Moreover, if the tilt of the cells are measured by a certain method in advance, the stage is beforehand moved to a position corresponding to the measured tilt, which enables the measurement for a shorter time.

On the other hand, to solve the problem "since the cells 34 tilt, the light radiated from the other end face 36 of the plugged honeycomb structure 31, which should be condensed toward the camera-side lens 2 by the field lens 11, proceeds away from the camera-side lens 2, and is not condensed by the camera-side lens 2", the following method is employed in another preferable configuration. That is, the camera-side lens and the field lens are preferably selected so as to establish a relation of "D/f>0.034" in which D is the effective diameter of the camera-side lens, and f is the focal length of the field lens. In consequence, even when the cells 34 of the plugged honeycomb structure 31 tilt as much as about 1° from the central axis as shown in FIG. 3A, at one image pickup in the constitution of FIG. 3A, the light radiated from the other end face of the plugged honeycomb structure is received by the camera, and the plugged state (the depths and defects of the plugged portions) can be inspected. At this time, to grasp more light tilted from the central axis in a case where a work (the plugged honeycomb structure) tilts, the effective diameter of the camera-side lens is preferably larger, and the focal length is preferably shorter in the field lens. In consequence, when the tilt of the work is presumed, the work has to be inspected as much as a plurality of times in accordance with the angle, but the number of the inspection times can be decreased, which enables the measurement for the shorter time.

2. Inspection Method of Plugged Honeycomb Structure:

An inspection method of the plugged honeycomb structure of the present invention is a method for inspecting the depths of the plugged portions and the defects (the plugged state) of the plugged portions of the plugged honeycomb structure by use of the above inspection device of the plugged honeycomb structure of the present invention.

In one embodiment of the inspection method of the plugged honeycomb structure of the present invention, the plugged state is inspected by using the above embodiment of the inspection device of the plugged honeycomb structure of the present invention shown in FIG. 1. Specifically, the plugged honeycomb structure is disposed between the light source and the camera-side lens so that one end face of the structure crosses, at right angles, a line connecting the light source to the camera-side lens (the one end face of the structure faces downwards in a vertical direction), the light is emitted from the light source to the one end face of the plugged honeycomb structure, and the light transmitted through the plugged portions of the plugged honeycomb structure and radiated from the other end face of the structure is condensed by the camera-side lens. The light condensed by the camera-side lens is received by the camera, and the image of the light received by the camera is processed by the image processor, to display the contrast (luminance) of the light transmitted through the plugged portions of the plugged honeycomb structure.

According to the inspection method of the plugged honeycomb structure of the present embodiment, the plugged honeycomb structure is inspected by using the embodiment of the inspection device of the plugged honeycomb structure of the present invention, whereby the depths and defects of the plugged portions can simultaneously be inspected for a short time and in a non-contact manner.

In another embodiment of the inspection method of the plugged honeycomb structure of the present invention, the plugged honeycomb structure is inspected by using another embodiment of the inspection device of the plugged honeycomb structure of the present invention as shown in FIG. 2. In still another embodiment of the inspection method of the plugged honeycomb structure of the present invention, the plugged honeycomb structure is inspected by using still another embodiment of the inspection device of the plugged honeycomb structure of the present invention as shown in FIG. 3A.

EXAMPLES

Hereinafter, the present invention will further specifically be described with respect to examples, but the present invention is not limited to these examples.

Example 1

As shown in FIG. 1, a light source was disposed so as to illuminate the upside in a vertical direction, a camera-side lens was disposed at a position of 860 mm from the light source above the light source in the vertical direction, and a camera was connected to an image processor above the camera-side lens in the vertical direction, whereby an inspection device of a plugged honeycomb structure was prepared. Constituent elements were fixed to a rack.

As the light source, a metal halide light source having a radiation angle α of 10° was used. As the camera-side lens, a CCTV lens having a diameter of 50 mm and a focal length of 100 mm was used. As the camera, a CCD camera having four million pixels was used. As the image processor, a personal computer and commercially available image processing software were used.

A plugged honeycomb structure prepared by the following method was an inspection target, and a plugged state (the depths and defects of the plugged portions) was inspected. To perform the inspection, the plugged honeycomb structure was disposed at a position of 10 mm above the light source (on the upside in the vertical direction) so that one end face of the structure crossed the vertical direction at right angles. The intensity of the light from the light source was set to 80000 lx.

Figure 6:
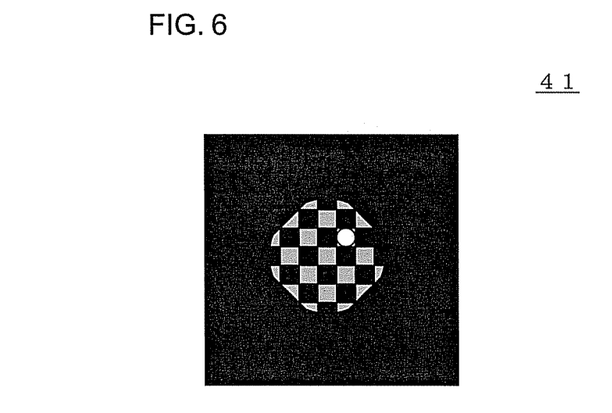
FIG. 6 is a schematic diagram showing that a plugged honeycomb structure is inspected by using an inspection device of the plugged honeycomb structure of Example 1, and showing the state of light transmitted through plugged portions.

Obtained results are shown in Table 1 and FIG. 6. In Table 1, a column of "an inspection region (%) at one image pickup" indicates the ratio of the area of the region which can be inspected at one image pickup with respect to the area of the end face of the plugged honeycomb structure. A column of "plug defects (places) in the whole work" indicates the number of the detected defects of the plugged portions. A column of "the number of inspection times per structure" indicates the number of the inspection times (the number of the times) required for inspecting one plugged honeycomb structure. FIG. 6 is a schematic diagram showing that the plugged honeycomb structure is inspected by using the inspection device of the plugged honeycomb structure of Example 1, and showing a state 41 of light transmitted through plugged portions.

(Preparation of Plugged Honeycomb Structure)

To 100 parts by mass of cordierite forming material obtained by combining a plurality of materials selected from the group consisting of talc, kaolin, calcinated kaolin, alumina, calcium hydroxide and silica and blending the materials at a predetermined ratio so that the chemical composition thereof were from 42 to 56 mass % of silica ($SiO_2$), from 30 to 45 mass % of alumina ($Al_2O_3$) and from 12 to 16 mass % of magnesia (MgO), from 12 to 25 parts by mass of graphite as a pore former and from 5 to 15 parts by mass of synthetic resin were added. Furthermore, after adding methyl celluloses and a surfactant in appropriate amounts, respectively, water was added to the materials to knead the materials, thereby preparing a kneaded clay. After vacuum-deaerating the prepared kneaded clay, the kneaded clay was extruded to obtain a formed honeycomb article. Next, the formed honeycomb article was fired to obtain a fired honeycomb article (a porous base member). Firing conditions were set to 1400 to 1430° C. and 10 hours. Next, the obtained fired honeycomb article was plugged. Open frontal areas of cells in one end face of the obtained fired honeycomb article were alternately masked in a checkered pattern, and the end of the article on a masked side was submerged into a plugging slurry containing a cordierite material as a ceramic material, whereby plugged portions alternately arranged in the checkered pattern were formed. Furthermore, as to the other end of the article, the cells each having one end plugged were masked, and plugged portions were formed in the same manner as in the formation of the plugged portions in the one end of the article. The fired honeycomb article provided with the plugged portions was dried and fired to obtain the plugged honeycomb structure. The obtained plugged honeycomb structure had a cylindrical shape having a bottom surface diameter of 140 mm and a length of 150 mm in a central axis direction, and had a partition wall thickness of 0.3 mm and a cell density of 31 cells/$cm^2$. Moreover, as to the obtained plugged honeycomb structure, the cells extended in the central axis direction of the plugged honeycomb structure, and both end faces of the structure were formed perpendicularly to the central axis.

It is seen from Table 1 and FIG. 6 that the light transmitted through the plugged portions is detected and that the plugged portions have four defects. In the inspection device of the plugged honeycomb structure of Example 1, a region of the end face of the plugged honeycomb structure which could be observed was small, and hence to observe (inspect) the whole end face of the plugged honeycomb structure, the camera-side lens and the camera were moved on an X-Y plane to perform the inspection.

TABLE 1

|  | Inspection region at one image pickup (%) | Plugged portion defects in the whole work (places) | Number of inspection times per structure |
|---|---|---|---|
| Example 1 | 0.6 | 4 | 167 |
| Example 2 | 25 | 4 | 4 |

The depths of the plugged portions were 10 mm. As to the depths of the plugged portions, a relation between the luminance of the light received by the camera and the plug depth was beforehand obtained by using a plugged honeycomb structure having known plugged portion depths to prepare an analytical curve, and the depths of the plugged portions were calculated based on the analytical curve. A relation between the depths (mm) of the plugged portions and the luminance (brightness in 256 gradations of 0 to 255) is shown in Table 2.

TABLE 2

| Depth of plugged portion (mm) | Luminance |
|---|---|
| 2 | 179 |
| 3 | 146 |
| 3.5 | 140 |
| 5 | 112 |
| 6 | 69 |
| 10 | 44 |

Example 2

As shown in FIG. 3A, a light source was disposed so as to illuminate the upside in a vertical direction, a field lens was disposed at a position of 450 mm from the light source above the light source in the vertical direction, a camera-side lens was disposed at a position of 410 mm from the field lens above the field lens in the vertical direction, and a camera was connected to an image processor, whereby an inspection device of a plugged honeycomb structure was prepared. Furthermore, the camera-side lens was fixed to the camera, and the inspection device was formed so that the camera-side lens and the camera could integrally move by an X-Y moving stage. Constituent elements (excluding the camera-side lens and the camera) were fixed to a rack. As the field lens, a plano-convex lens having a diameter of 200 mm and a focal length of 500 mm was used. As the X-Y moving stage, a stage having a stroke of 100 mm was used. The light source, the camera-side lens, the camera and the image processor similar to those of Example 1 were used.

Figure 7:
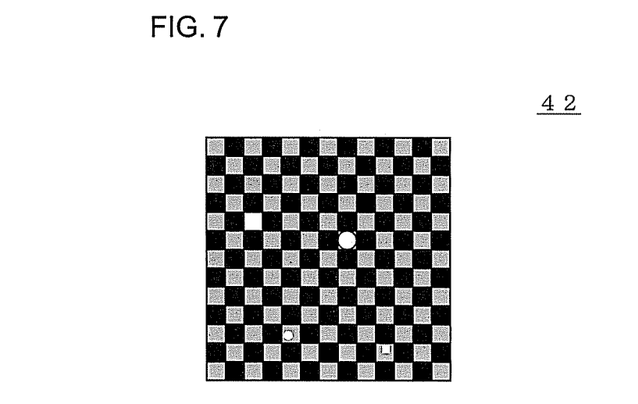
FIG. 7 is a schematic diagram showing that a plugged honeycomb structure is inspected by using an inspection device of the plugged honeycomb structure of Example 2, and showing the state of light transmitted through plugged portions.

The plugged state of the plugged honeycomb structure was inspected in the same manner as in Example 1. Obtained results are shown in Table 1 and FIG. 7. FIG. 7 is a schematic diagram showing that a plugged honeycomb structure is inspected by using an inspection device of the plugged honeycomb structure of Example 2, and showing a state 42 of light transmitted through plugged portions.

It is seen from Table 1 and FIG. 7 that the whole end face of the plugged honeycomb structure can be observed and that the plugged portions have four defects.

Figure 8:
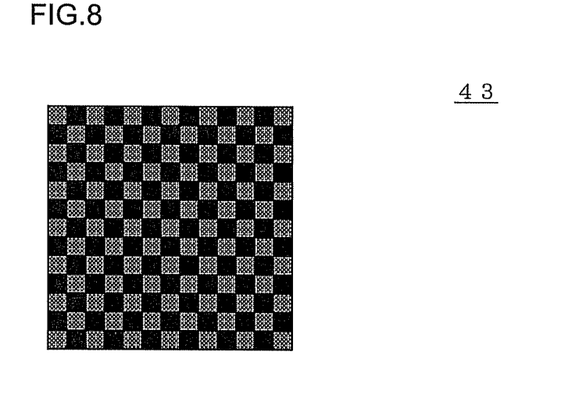
FIG. 8 is a schematic diagram showing that the plugged honeycomb structure is inspected by using the inspection device of the plugged honeycomb structure of Example 2, and showing the state of the light transmitted through the plugged portions.

Moreover, the plugged honeycomb structure was inspected by using the inspection device of the plugged honeycomb structure of Example 2 while varying the tilt of the disposed plugged honeycomb structure. Results are shown in FIG. 8. FIG. 8 shows inspection results (is a schematic diagram showing a state 43 of light transmitted through the plugged portions) in a case where the plugged honeycomb structure is disposed in a state in which the central axis of the structure tilts as much as 5° from the vertical direction (a state in which the light condensed by the field lens is not directed to the camera-side lens but deviates from the camera-side lens (see FIG. 3A)). Moreover, FIG. 7 shows inspection results (is a schematic diagram showing the state 42 of the light transmitted through the plugged portions) in a case where the plugged honeycomb structure is disposed in a state in which the central axis of the structure tilts as much as 5° from the vertical direction and the camera-side lens and the camera are moved to a position suitable for observation by the X-Y moving stage as shown in FIG. 3B.

It is seen from FIGS. 7 and 8 that when the cells of the plugged honeycomb structure tilt from the vertical direction, the state of the plugged portions cannot sufficiently be observed, whereas when the camera-side lens and the camera are moved to the position suitable for the observation by the X-Y moving stage, the state of the plugged portions can satisfactorily be observed.

Example 3

An inspection device of a plugged honeycomb structure was prepared in the same manner as in Example 2 except that a CCTV lens having an effective diameter of 8.7 mm was used as a camera-side lens. A ratio "D/f" was 0.017 in which D was the effective diameter of the camera-side lens and f was the focal length of the field lens. By use of the obtained inspection device of the plugged honeycomb structure, "a corresponding tilt limit)(°)" was measured, and "the number of inspection times" was calculated on trial by the following method. Results are shown in Table 3.

(Corresponding Tilt Limit)

The defects of plugged portions were inspected by using the inspection device of the plugged honeycomb structure in the same manner as in the above "method for inspecting "the defects of the plugged portions" by use of the inspection device of the plugged honeycomb structure of Example 1" except that the plugged honeycomb structure was inspected as much as a plurality of times while tilting the structure stepwise. Moreover, the tilt range of the plugged honeycomb structure in which the inspection of "the defects of the plugged portions" could be performed was obtained. Then, the maximum tilt with which the inspection of "the defects of the plugged portions" could be performed was obtained as "the corresponding tilt limit)(°)".

(Number of Inspection Times)

On the assumption of the inspection of the plugged honeycomb structure in which the cells might tilt within ±1°, the number of the inspection times necessary for inspecting "the defects of the plugged portions" was calculated on trial. The trial calculation method of the number of the inspection times will be described with respect to Example 3 as follows. First, the smallest circumscribed square (a square with one side of 2) is provided with respect to a circle having a radius of 1 in a case where the corresponding region of the plugged honeycomb structure in which the cells might tilt ±1° is assumed. Next, the largest inscribed square (a square with one side of 0.7) is provided with respect to a circle having a radius of 0.5 in a case where the tilt corresponding region ±0.5° possible in Example 3 is assumed. In addition, the number of the largest inscribed squares (each square with one side of 0.7) which can fill in the smallest circumscribed square (the square with one side of 2) is calculated for the trial calculation. Then, in the case of Example 3, calculation "(2×2)/(0.7×0.7)=8.16" is performed, and the obtained value (8.16) is rounded out after the decimal point to obtain the number of the inspection times of "9".

TABLE 3

|  | D/f | Corresponding tilt limit (°) | Number of inspection times |
|---|---|---|---|
| Example 3 | 0.017 | 0.5 | 9 |
| Example 4 | 0.024 | 0.7 | 4 |
| Example 5 | 0.034 | 1 | 1 |
| Example 6 | 0.069 | 2 | 1 |

Example 4

An inspection device of a plugged honeycomb structure was prepared in the same manner as in Example 2 except that a CCTV lens having an effective diameter of 12.2 mm was used as a camera-side lens. A ratio "D/f" was 0.024 in which D was the effective diameter of the camera-side lens and f was the focal length of a field lens. By use of the obtained inspection device of the plugged honeycomb structure, "a corresponding tilt limit)(°)" was measured, and "the number of inspection times" was calculated on trial by the above method. Results are shown in Table 3.

Example 5

An inspection device of a plugged honeycomb structure was prepared in the same manner as in Example 2 except that a CCTV lens having an effective diameter of 17.5 mm was used as a camera-side lens. A ratio "D/f" was 0.034 in which D was the effective diameter of the camera-side lens and f was the focal length of a field lens. By use of the obtained inspection device of the plugged honeycomb structure, "a corresponding tilt limit)(°)" was measured, and "the number of inspection times" was calculated on trial by the above method. Results are shown in Table 3.

Example 6

An inspection device of a plugged honeycomb structure was prepared in the same manner as in Example 2 except that a CCTV lens having an effective diameter of 34.9 mm was used as a camera-side lens. A ratio "D/f" was 0.069 in which D was the effective diameter of the camera-side lens and f was the focal length of a field lens. By use of the obtained inspection device of the plugged honeycomb structure, "a corresponding tilt limit)(°)" was measured, and "the number of inspection times" was calculated on trial by the above method. Results are shown in Table 3.

It is seen from Table 3 that the limit of the tilt when the plugged honeycomb structure which can be detected increases, as the value of "D/f" is large. It can also be confirmed that the number of the inspection times can be one in "D/f>0.034". Moreover, in Examples 1 to 6, an area sensor camera was used as the CCD camera, but even if a line sensor camera was used, a similar result could be obtained.

Examples 7 to 22

An inspection device of a plugged honeycomb structure was prepared in the same manner as in Example 6 except that the radiation angle α of a light source was varied as shown in Table 4 (Examples 7 to 22). The plugged state of the plugged honeycomb structure was inspected by use of the obtained inspection device of the plugged honeycomb structure in the same manner as in Example 1. It is to be noted that when the plugged state of the plugged honeycomb structure was inspected, the plugged honeycomb structure was disposed in a state in which the central axis of the structure tilted as much as 0° (θ=0°), 1° (θ=1°) and 2° (θ=2°) from a vertical direction, and the inspections were performed with respect to the respective angles. Moreover, as evaluation in the inspection of the plugged state of the plugged honeycomb structure, "the appearance of the defect" was evaluated, a case where the defect could remarkably satisfactorily be observed was "A", a case where the defect could satisfactorily be observed was "B", and a case where the defect could be observed but was blurred slightly was "C".

TABLE 4

|  | Radiation angle α (°) | Appearance of defect | | |
|---|---|---|---|---|
|  |  | θ = 0° | θ = 1° | θ = 2° |
| Example 7 | 0 | A | C | C |
| Example 8 | 1 | A | A | C |
| Example 9 | 2 | A | A | A |
| Example 10 | 3 | A | A | A |
| Example 11 | 4 | A | A | A |
| Example 12 | 5 | A | A | A |
| Example 13 | 6 | B | B | B |
| Example 14 | 7 | B | B | B |
| Example 15 | 8 | B | B | B |
| Example 16 | 9 | B | B | B |
| Example 17 | 10 | B | B | B |
| Example 18 | 11 | C | C | C |
| Example 19 | 12 | C | C | C |
| Example 20 | 13 | C | C | C |
| Example 21 | 14 | C | C | C |
| Example 22 | 15 | C | C | C |

It is seen from Table 4 that when the radiation angle α is not less than "the angle (the tilt of the cell) θ formed by a line crossing the one end face of the plugged honeycomb structure at right angles and the cells (the cells of the plugged honeycomb structure)" and the radiation angle α is 5° or less, the defects of the plugged portions can remarkably satisfactorily be detected. It is also seen that when the radiation angle α is larger than 5° and 10° or less, the defects can satisfactorily be detected. It is further seen that when the radiation angle α is smaller than "the angle θ formed by the line crossing the one end face of the plugged honeycomb structure at right angles and the cells (the cells of the plugged honeycomb structure)", the amount of the light decreases, and the defects can be detected, but the defects have a slightly blurred state. It is also seen that when the radiation angle α exceeds 10°, the amount of the light decreases, and the defects can be detected, but the defects have a slightly blurred state.

The inspection device of the plugged honeycomb structure and the inspection method of the plugged honeycomb structure of the present invention can preferably be utilized for the manufacturing of the plugged honeycomb structure in order to obtain the plugged honeycomb structure having satisfactory plugged portion states.

What is claimed is:

1. An inspection device of a plugged honeycomb structure in which the cylindrical plugged honeycomb structure having porous partition walls to partition a plurality of cells extending through the structure from one end face to the other end face thereof and having plugged portions at the ends of the cells is an inspection target, the inspection device comprising:

a light source which illuminates the one end face of the plugged honeycomb structure as the inspection target;

a camera-side lens which condenses light emitted from the light source to the one end face, transmitted through the plugged portions of the plugged honeycomb structure and radiated from the other end face;

a camera which receives the light condensed by the camera-side lens; and an image processor which processes an image of the luminance of the transmitted light received by the camera to display the contrast of the luminance of the transmitted light transmitted through the plugged portions of the plugged honeycomb structure, which luminance is indicative of at least one of the depth of the plugged portions and a defect in one or more of the plugged portions.

2. The inspection device of the plugged honeycomb structure according to claim 1, further comprising:

a field lens disposed between the honeycomb structure and the camera-side lens to condense, toward the camera-side lens, the amount of light transmitted through the plugged portions of the honeycomb structure and radiated from the other end face, wherein the light condensed by the field lens is further condensed by the camera-side lens, and received by the camera.

3. The inspection device of the plugged honeycomb structure according to claim 2, further comprising:

an X-Y moving stage to which the camera and the camera-side lens are attached and which moves the camera and the camera-side lens in a plane substantially parallel to the end face of the plugged honeycomb structure on such a side as to radiate the light.

4. The inspection device of the plugged honeycomb structure according to claim 2, wherein a relation of "D/f>0.034" is established in which D is the effective diameter of the camera-side lens, and f is the focal length of the field lens.

5. The inspection device of the plugged honeycomb structure according to claim 3, wherein a relation of "D/f>0.034" is established in which D is the effective diameter of the camera-side lens, and f is the focal length of the field lens.

6. The inspection device of the plugged honeycomb structure according to claim 1, wherein the light emitted from the light source to the one end face of the plugged honeycomb structure is light which spreads at a specific radiation angle, and the radiation angle has a size which is not less than an angle formed by a line crossing the one end face of the plugged honeycomb structure at right angles and the cells.

7. The inspection device of the plugged honeycomb structure according to claim 6, wherein the radiation angle is 10° or less.

8. An inspection method of the plugged honeycomb structure which inspects the depths and defects of the plugged portions of the plugged honeycomb structure by use of the inspection device of the plugged honeycomb structure according to claim 1.

* * * * *

UNITED STATES PATENT AND TRADEMARK OFFICE
CERTIFICATE OF CORRECTION

PATENT NO. : 8,421,857 B2
APPLICATION NO. : 12/718221
DATED : April 16, 2013
INVENTOR(S) : Takayoshi Akao, Akihiro Mizutani and Kensuke Tanaka It is certified that error appears in the above-identified patent and that said Letters Patent is hereby corrected as shown below:

Title Page, Item (56), References Cited, U.S. PATENT DOCUMENTS add: "2007/0132988 A1* 6/2007 Gargano et al. 356/237.6"

Signed and Sealed this
Twenty-fifth Day of June, 2013

Teresa Stanek Rea
*Acting Director of the United States Patent and Trademark Office*